(12) United States Patent
Choi et al.

(10) Patent No.: US 11,272,868 B2
(45) Date of Patent: Mar. 15, 2022

(54) POTENTIOMETRIC WEARABLE SWEAT SENSOR

(71) Applicant: The Johns Hopkins University, Baltimore, MD (US)

(72) Inventors: Dong-Hoon Choi, Baltimore, MD (US); Peter Searson, Baltimore, MD (US); Garry R. Cutting, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 487 days.

(21) Appl. No.: 16/099,176

(22) PCT Filed: May 4, 2017

(86) PCT No.: PCT/US2017/031031
§ 371 (c)(1),
(2) Date: Nov. 5, 2018

(87) PCT Pub. No.: WO2017/192836
PCT Pub. Date: Nov. 9, 2017

(65) Prior Publication Data
US 2019/0209062 A1    Jul. 11, 2019

Related U.S. Application Data

(60) Provisional application No. 62/332,949, filed on May 6, 2016.

(51) Int. Cl.
*A61B 5/05* (2021.01)
*A61B 5/145* (2006.01)
(Continued)

(52) U.S. Cl.
CPC ........ *A61B 5/14546* (2013.01); *A61B 5/0537* (2013.01); *A61B 5/1477* (2013.01);
(Continued)

(58) Field of Classification Search
CPC ............ A61B 5/14517; A61B 5/14546; A61B 5/6833; G01N 27/4035; G01N 27/403; G01N 27/4161
See application file for complete search history.

(56) References Cited

U.S. PATENT DOCUMENTS 9,125,625 B2    9/2015 Wang
2010/0044224 A1    2/2010 Kataky
(Continued)

FOREIGN PATENT DOCUMENTS

WO    WO 2015/198668 A1    12/2015

OTHER PUBLICATIONS

Bandodkar, Amay J. et al.: "*Epidermal tattoo potentiometric sodium sensors with wireless signal transduction for continuous non-invasive sweat monitoring*"; Biosensors and Bioelectronics, vol. 54, 2014, pp. 603-609, XP055298222.
(Continued)

*Primary Examiner* — Christian Jang
(74) *Attorney, Agent, or Firm* — DLA Piper LLP (US)

(57) ABSTRACT

A potentiometric sensor that includes a housing and working electrode is provided. The housing includes a reference electrode, a first hydrogel containing hydrogel that contains a reference solution, and a salt bridge. The sensor is wearable and can be used for continuous on-body sweat measurements.

11 Claims, 13 Drawing Sheets

(51) Int. Cl.
  *G01N 27/403* (2006.01)
  *A61B 5/0537* (2021.01)
  *A61B 5/1477* (2006.01)
  *A61B 5/00* (2006.01)
  *G01N 27/416* (2006.01)

(52) U.S. Cl.
  CPC ........ *A61B 5/14517* (2013.01); *A61B 5/6833* (2013.01); *G01N 27/4035* (2013.01); *G01N 27/4161* (2013.01); *A61B 2562/0209* (2013.01); *A61B 2562/125* (2013.01)

(56) References Cited

U.S. PATENT DOCUMENTS

| | | | |
|---|---|---|---|
| 2011/0027458 A1* | 2/2011 | Boock | A61B 5/14532 427/9 |
| 2012/0217173 A1* | 8/2012 | Bar-Or | G01N 33/49 205/792 |
| 2013/0144131 A1 | 6/2013 | Wang | |
| 2014/0012114 A1* | 1/2014 | Zevenbergen | G01N 33/48707 600/346 |
| 2017/0122899 A1* | 5/2017 | Sakata | G01N 27/4145 |

OTHER PUBLICATIONS

Choi, Dong-Hoon et al.: "*Wearable Potentiometric Chloride Sweat Sensor: The Critical Role of the Salt Bridge*"; Analytical Chemistry, Nov. 29, 2016, vol. 88, No. 24, pp. 12241-12247, XP055629862.

Dam, V. A. T. et al.: "*Toward wearable patch for sweat analysis*"; Sensors and Actuators B: Chemical, Feb. 4, 2016, vol. 236, pp. 834-838, XP029700006.

Extended European Search Report dated Oct. 18, 2019, regarding EP 17 79 3331.

Gonzalo-Ruiz, Javier et al.: "*Early determination of cystic fibrosis by electrochemical chloride quantification in sweat*"; Biosensors and Bioelectronics, Feb. 15, 2009, vol. 24, No. 6, pp. 1788-1791, XP025922759.

\* cited by examiner

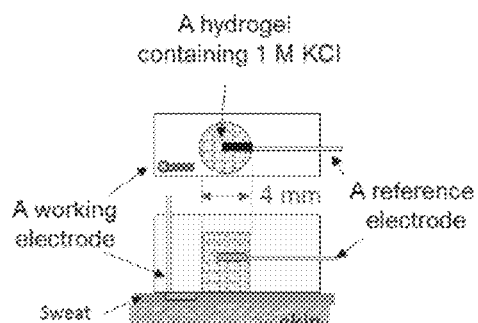 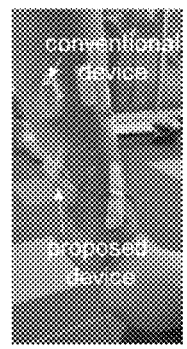 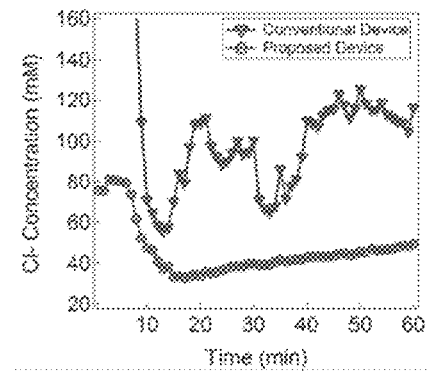
FIG. 10A        FIG. 10B        FIG. 10C
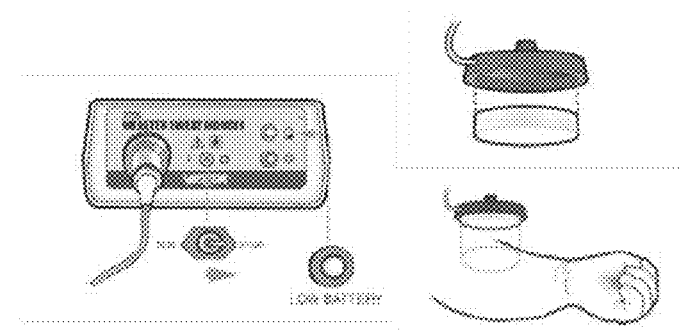 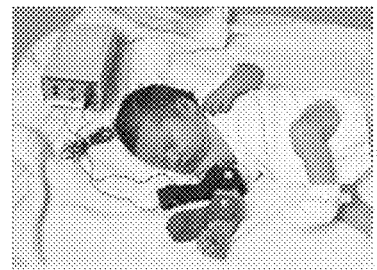
FIG. 11A
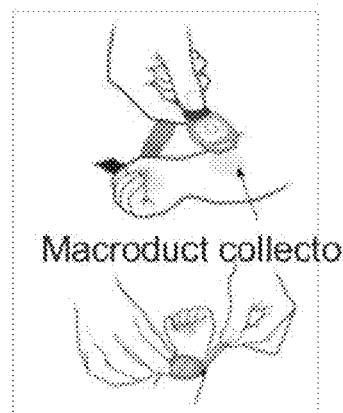 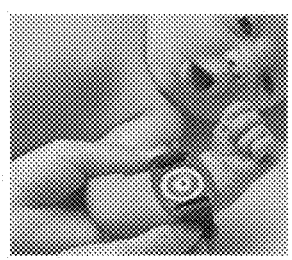 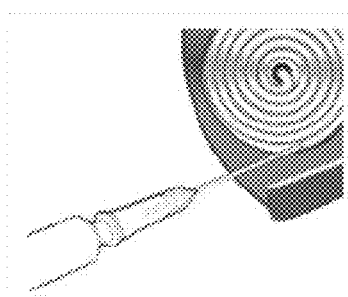
FIG. 11B

POTENTIOMETRIC WEARABLE SWEAT SENSOR

CROSS-REFERENCE TO RELATED APPLICATIONS

This application is a 35 USC § 371 National Stage application of International Application No. PCT/US2017/031031 filed May 4, 2017, which claims the benefit under 35 USC § 119(e) to U.S. Application Ser. No. 62/332,949 filed May 6, 2016. The disclosure of each of the prior applications is considered part of and is incorporated by reference in the disclosure of this application.

FIELD OF THE INVENTION

The present invention relates to a potentiometric sensor for measuring the concentration of chloride ions in sweat.

BACKGROUND OF THE INVENTION

Potentiometric sensing is a method developed to measure the concentration of an ion in solution. This method measures the electrical potential difference between a reference and a working electrode (FIG. 1). The potential of the reference electrode should be constant. The potential of the working electrode is dependent on the concentration of the ion in solution. In order to detect chloride ions, a Ag/AgCl electrode is used as the working electrode. The measured potential is converted to a concentration by measuring the potential for a range of solutions of known concentration. This calibration curve is then used to determine the concentration of an unknown test solution.

Sweat chloride is a biomarker for cystic fibrosis (CF) and for electrolyte loss during exercise. The chloride ion concentration in the sweat of CF patients is typically 60 to 150 mM, much higher than in healthy individuals (typically 10-40 mM), and hence sweat chloride testing is the most widely used assay for diagnosis of CF. The assay involves collection of a sweat sample and analysis by coulometric titration, manual titration, or an ion selective electrode. Chloride is the most abundant ion in sweat, and hence is also a potential biomarker for electrolyte loss. The successful development of a wearable sweat chloride sensor can reduce the cost and time for laboratory-based sweat testing for CF patients, and can provide real-time information for healthy individuals during exercise.

The development of wearable sensors to measure biomarkers in sweat is recognized as a major technological challenge. There are three main candidate technologies for wearable sweat chloride sensors: titration devices, conductivity measurements, and potentiometric sensors. Wearable titration sensors have been reported, but require subsequent analysis on a separate instrument. Wearable conductivity sensors are readily miniaturized, but are not chloride specific. Potentiometric measurements rely on the relationship between the ion concentration and the electrochemical potential of an electrode. This is a well-established analytical technique that can be readily miniaturized. Chloride ion detection relies on the equilibrium between chloride ions and silver chloride ($AgCl(s)+e-\leftrightarrow Cl-(aq)+Ag(s)$), and can be measured using silver chloride electrodes that are widely employed in electrophysiology and analytical chemistry. There are relatively few examples of wearable sodium and potassium ion sweat sensors that use ion selective membranes, and wearable potentiometric chloride sensors.

Two publications describing miniaturized chloride sweat sensors are described (see below). Gonzalo-Ruiz et al. reports measurements immediately after inducing sweat in subjects but does not report measurements as a function of time. Lynch et al. reports only measurements in a test solution; neither reference reports any on-body measurements. Furthermore, neither reference reports the time response of its device.

Gonzalo-Ruiz's apparatus is used to sense chloride ions in sweat. The apparatus includes a screen-printed Ag/AgCl electrode covered by pHEMA hydrogel matrix containing KCl (the hydrogel matrix was used as a reservoir for the reference solution) as the reference electrode, a screen-printed Ag/AgCl electrode as the working electrode, and two other electrodes (cathode and anode) for sweat generation (FIG. 2).

Lynch's apparatus is used to sense chloride, potassium, and sodium ions in a sweat sample. The apparatus is not wearable. The components for chloride ion sensing include a Ag/AgCl electrode covered by a hydrogel containing the reference solution as the reference electrode and a Ag/AgCl electrode as the working electrode (FIG. 3).

In current designs of wearable sweat sensors (chloride ions as well as other ions) the reference electrode is covered with a gel containing the reference solution. Transport of ions between the reference solution and test solution (sweat) results in changes in the potential of the working electrode and results in measurement error. As a result, these devices cannot be used for continuous on-body measurements. Thus, there is a need for sweat sensors that are suitable for continuous on-body measurements.

SUMMARY OF THE INVENTION

The present invention is based on the discovery that a sweat chloride sensor integrated with a salt bridge minimizes equilibration and enables stable measurements over extended periods of time.

One embodiment of the present invention is to provide a potentiometric sensor that includes a housing and a working electrode. The housing includes a reference electrode, a first hydrogel that contains a reference solution, and a salt bridge.

In another embodiment, the salt bridge includes a second hydrogel.

In another embodiment, the first and second hydrogels are the same.

In another embodiment, the hydrogel is agarose.

In another embodiment, the housing includes polydimethylsiloxane (PDMS).

In another embodiment, the reference and working electrodes are Ag/AgCl electrodes.

In another embodiment, the reference solution includes 1M KCl.

In another embodiment, the salt bridge includes an ion selective polymer.

In another embodiment, the ion selective polymer is Nafion or polydiallyldimethylammonium chloride (polyDADMAC).

In another embodiment, the sensor monitors the concentration of an ion in sweat.

In another embodiment, the sensor is wearable.

In another embodiment, the ion is selected the ion can be chloride, potassium or sodium.

In another embodiment, the sensor is used to monitor chloride ion concentration in a cystic fibrosis (CF) subject.

In another embodiment, the sensor is used to monitor chloride ion concentration as a function of workout intensity.

Another embodiment of the present invention is to provide a method of measuring an ion concentration in sweat. The method includes a step of placing a potentiometric sensor on the skin of a subject. The potentiometric sensor includes a reference electrode, a first hydrogel containing a reference solution, a salt bridge, and a working electrode. The salt bridge is in direct contact with the skin. Another step includes generating sweat under the salt bridge. The ions in the sweat form an ionic circuit between the reference electrode and the working electrode. A third step includes measuring a potential difference proportional to the ion concentration in the sweat, thereby measuring the ion concentration.

In another embodiment, the salt bridge used in the method includes a second hydrogel.

In another embodiment, the step of measuring the ion concentration is continuous.

In another embodiment, the ion being measured can be chloride, potassium or sodium.

In another embodiment, the ion being measure is chloride.

In another embodiment, the method includes the step of diagnosing whether the subject has cystic fibrosis (CF) based upon the chloride ion concentration.

In another embodiment, the method includes assessing an intensity of a workout based upon the chloride ion concentration.

Other aspects and advantages of the invention will be apparent from the following description and the appended claims.

BRIEF DESCRIPTION OF THE DRAWINGS

FIGS. 10A-10C. Comparison between the sweat sensor described in this ROI and a sweat sensor fabricated to mimic the devices described in Gonzalo-Ruiz et al. 2009 and Lynch et al. 2002. (a) Design of sweat sensor used to mimic the devices in Gonzalo-Ruiz et al. 2009 and Lynch et al. 2002, (b) photograph of an on-body test, and (c) chloride concentrations measured by the device described in this ROI and the device fabricated to mimic the sensors reported in Gonzalo-Ruiz et al. 2009 and Lynch et al. 2002.

FIGS. 11A-11B. Microduct® sweat collection system (a) Webster sweat inducer, and (b) Macroduct collector. (Macroduct sweat collection system)

DETAILED DESCRIPTION OF THE INVENTION

Other aspects and advantages of the invention will be apparent from the following description.

A challenge in developing wearable potentiometric sensors is that equilibration between the reference solution and the test solution over time results in a measurement error. In recent work, the critical role of the salt bridge in determining the sensor performance has been reported. An analytical model to assess the rate of equilibration between the reference and test solutions, and hence to predict the measurement error as a function of salt bridge geometry was used. The model was validated by a series of parametric studies, which allowed the design of rules for specific applications. The present invention uses these criteria to design and optimize a wearable thin film chloride sweat sensor. Building on previous work, the present invention makes the following key advances: (1) a fabrication process to integrate the salt bridge into a thin film sensor is described; (2) the reliability and reproducibility of the sensor is described; and (3) and in vivo results from in vivo testing which indicate that sweat chloride concentration is dependent on exercise intensity are presented. The device is fabricated on a plastic substrate and can be easily and comfortably worn on the body using a commercial adhesive bandage. The device shows reliable performance over 12 hours. The accuracy of the device is evaluated over the concentration range of about 10 to 150 mM, and the calibration curve and dose response of the fabricated devices are also presented. Finally, the concentration changes during an exercise with graded exercise load are presented.

To overcome problems discussed in the Background of the Invention section, a salt bridge between the reference solution and the working electrode and test solution was introduced. The present invention describes a sweat sensor to reliably measure the concentration of chloride ions in sweat. By introducing a salt bridge, ion transport between the reference solution and test solution is very slow and hence the potential of the reference electrode remains constant for extended times. Therefore, reliable on-body measurements can be made over time.

Figure 12:
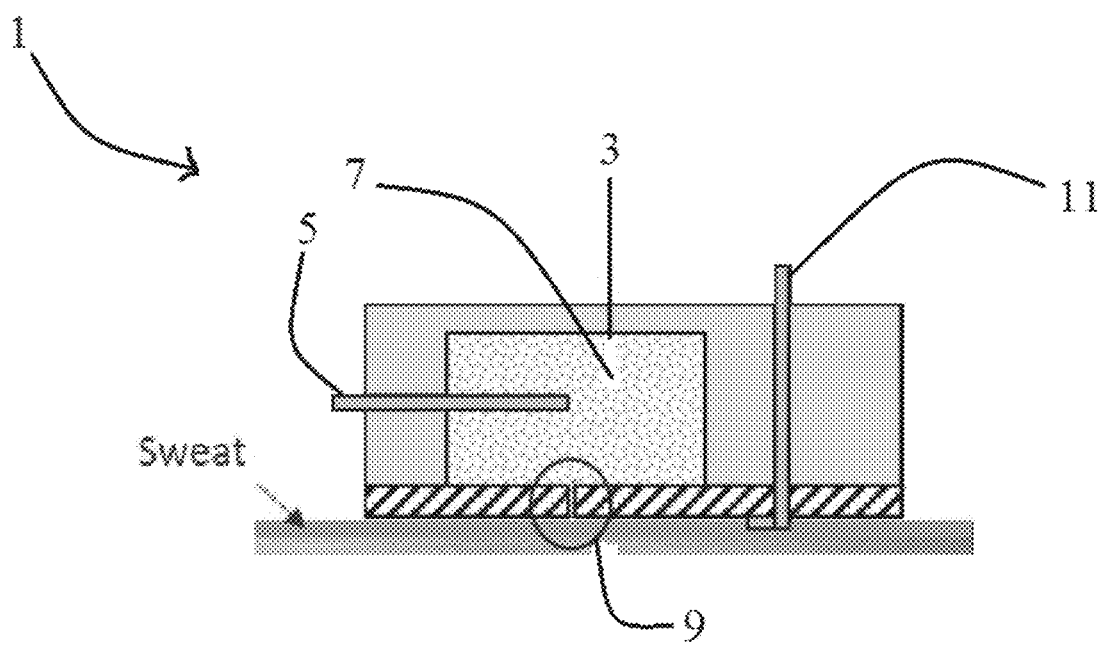
FIG. 12. An illustration of potentiometric sensor components.
Figure 13A:
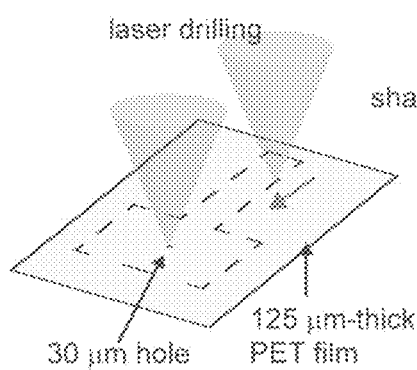
FIGS. 13A-13F. Fabrication of a thin film, wearable, potentiometric sweat chloride sensor. (A) Laser drilling of a 30 μm hole that defines the salt bridge. (B-C) E-beam evaporation of a 10 nm Cr adhesion layer and 300 nm Ag film. (D) Chloridization of the Ag layer in 50 mM $FeCl_3$ solution. (E) The reference solution gel is introduced into the salt bridge and on top of the substrate. (F) The reference solution gel is sealed using a UV curable resin.
Figure 13B:
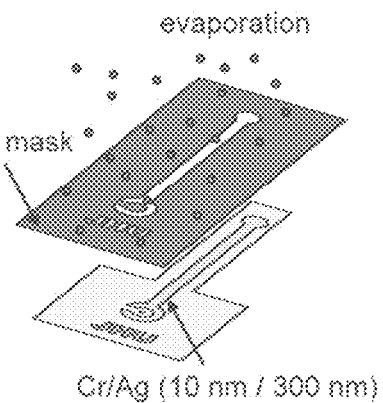
Figure 13C:
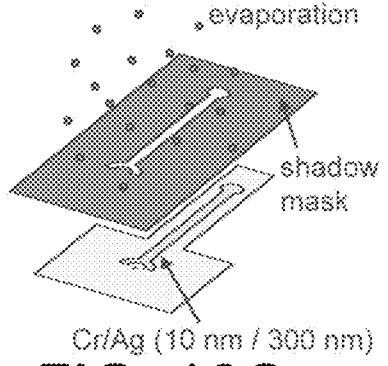
Figure 13D:
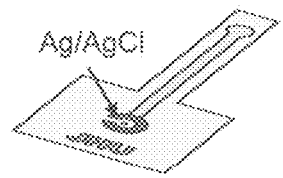
Figure 13E:
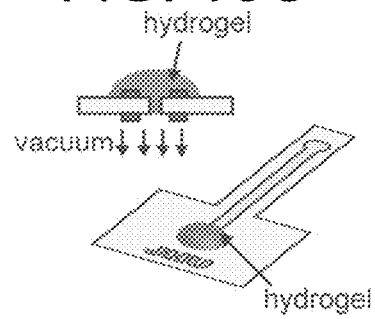
Figure 13F:
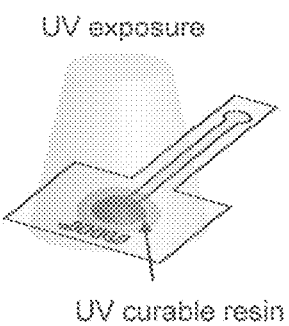

FIG. 12 illustrates the potentiometric sensor 1 components. The potentiometric sensor includes a housing 3 and working electrode 11. The housing includes a reference electrode 5, a first hydrogel that contains a reference solution 7, and a salt bridge 9.

Figure 1:
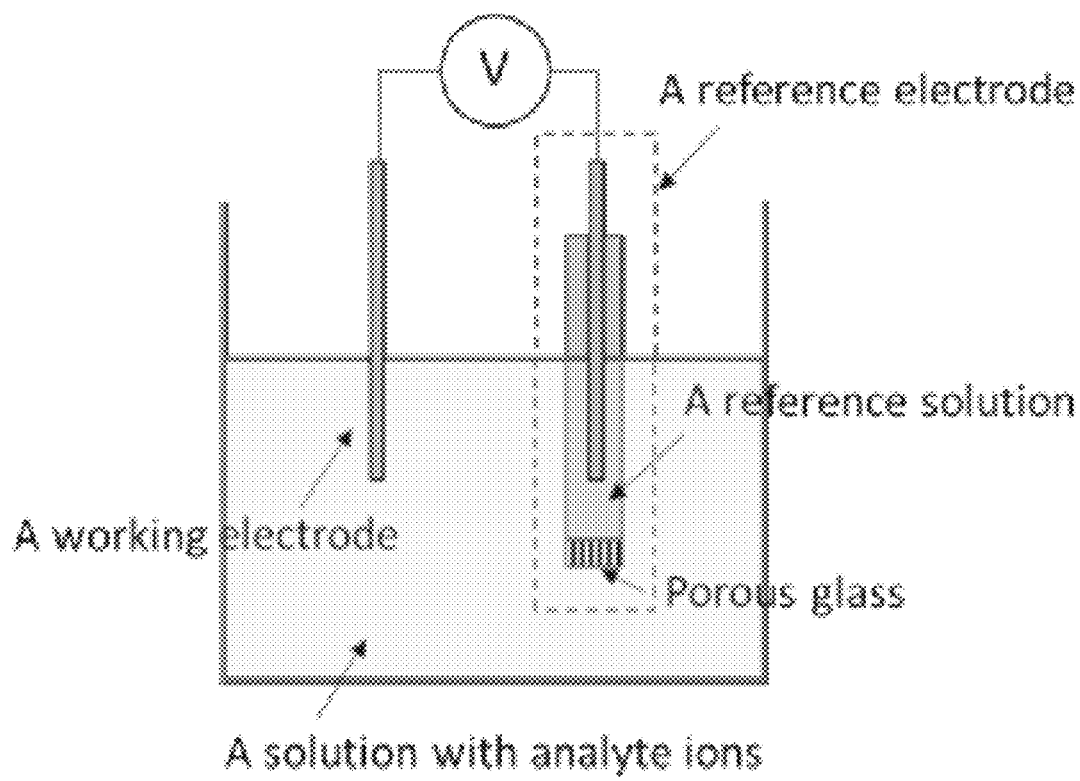
FIG. 1. Potentiometric measurement.
Figure 2A:
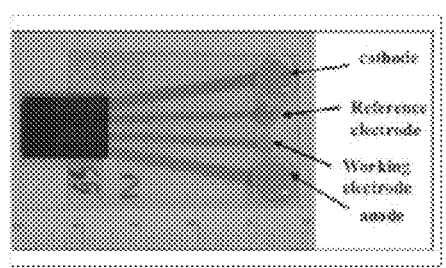
FIGS. 2A-2B. Potentiometric sensor for measurement of chloride ions in sweat (a) Photograph of fabricated sweat sensor (b) Schematic view of working electrode and reference electrode. Note that the gel containing the reference solution reservoir has a large contact area with the test solution. This results in rapid transport between the reference solution and test solution, which also results in a change in the potential of the reference electrode.
Figure 2B:
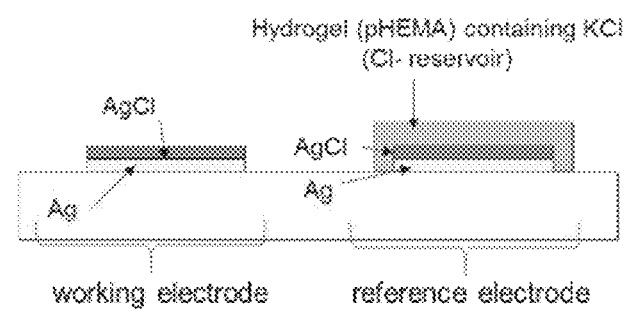
Figure 3:
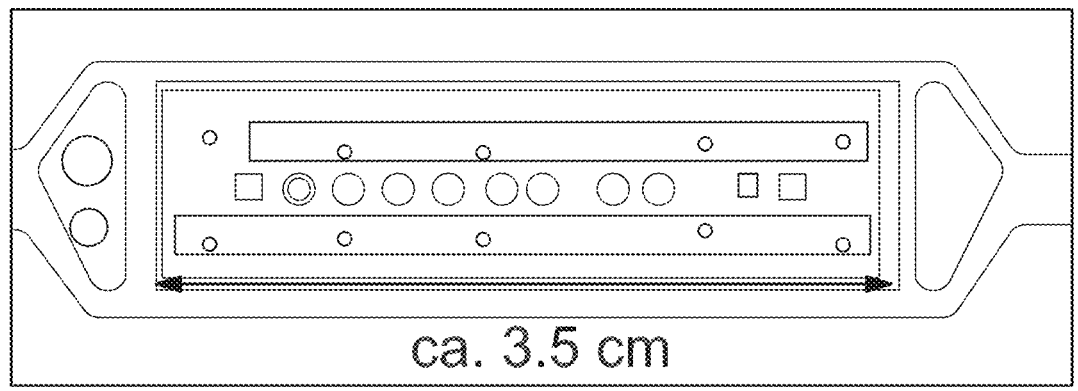
FIG. 3. Sensor array to detect chloride, potassium, and sodium ions in sweat.
Figure 4A:
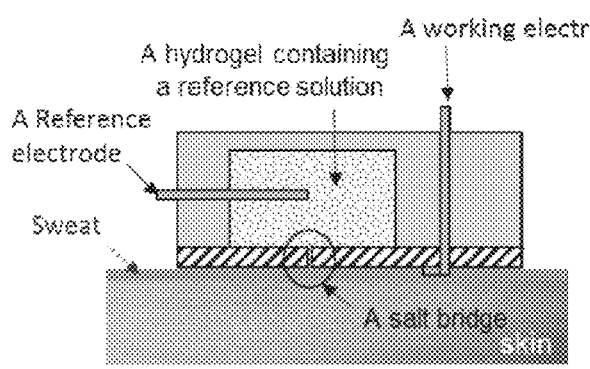
FIG. 4A-4B. (a) Proposed sweat sensor with a salt bridge, (b) salt bridge geometry.
Figure 4B:
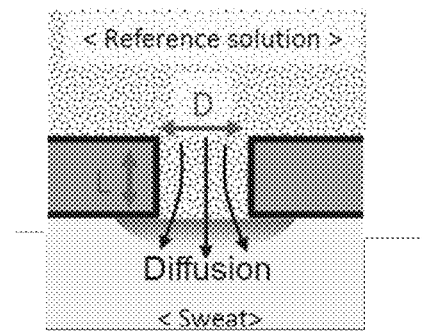

As shown in FIG. 4(*a*), the proposed sweat sensor in this invention consists of: (1) a reference electrode (a Ag/AgCl electrode), (2) a hydrogel containing a reference solution, (3) a salt bridge filled with the hydrogel and designed to minimize ion transport between the reference solution and test solution, (4) a working electrode (a Ag/AgCl electrode), and (5) an integrated package to optimize sweat measurements.

On generation of sweat under the sensor, the ionic circuit between the working electrode and the reference electrode is completed, resulting in a potential difference that is related to the chloride ion concentration in sweat. Using a calibration curve determined for the sensor prior to use, the potential difference can be related directly to a chloride concentration.

Transport of ions between the reference solution and the test solution (sweat) is dependent on the salt bridge geometry, and the materials used in the sensor. The design of the sensor has been optimized to minimize ion transport and maximize the time of measurement. Designs using an ion selective polymer for the salt bridge have been tested.

Parametric Studies

To optimize the geometry of the salt bridge, parametric studies have been performed.

Figure 5A:
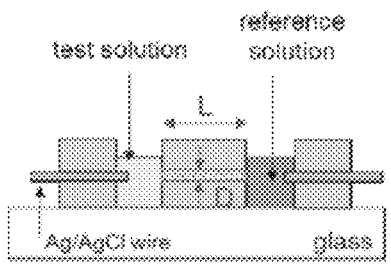
FIGS. 5A-5B. Parametric studies (a) A schematic view of a test device for parametric studies, and (b-c) measured output voltage as a function of a time according to (a) the length of the salt bridge (L=0.9, 2.8, 4.8, and 10.4 mm, D=635 μm) and the diameter of the salt bridge (D=100 mm, 150, 380, and 635 μm).
Figure 5B:
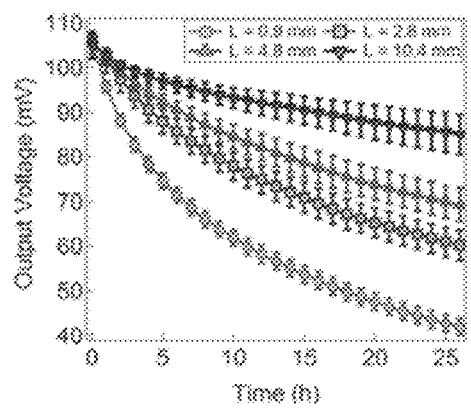
Figure 5C:
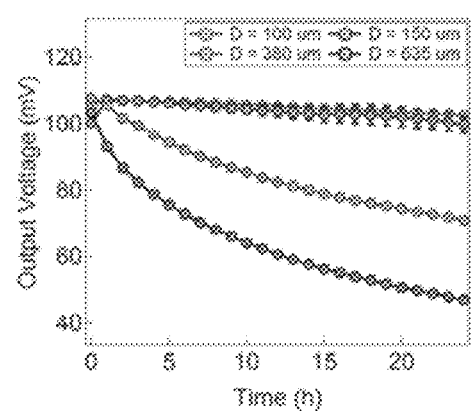

FIG. 5 (*a*) shows a schematic view of a test device for parametric studies. The test device has two chambers (a reference and a test chamber) and the chambers are connected by a salt bridge. The reference and test chambers are filled with a reference solution of 1M KCl and a test solution of 10 mM NaCl, respectively. Numerous devices with different salt bridge geometries were tested, and then their voltage drift were compared.

FIG. 5 (*b-c*) show the results. As the salt bridge is longer, the voltage drift decreases (FIG. 5(*b*)). Also, the voltage drift is reduced as the salt bridge diameter decreases (FIG. 5(*c*)).

Figure 6A:
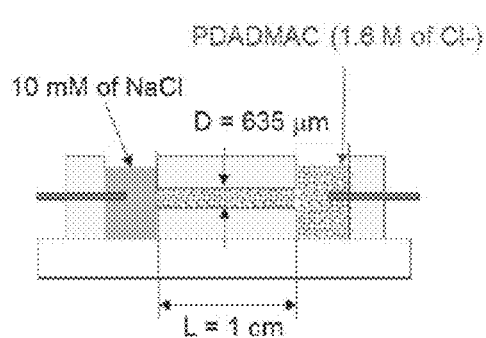
FIGS. 6A-6B. (a) A test device adopting an ion selective polymer poly(diallyldimethylammonium chloride) (pDADMAC) for the salt bridge, (b) Measured output voltage.
Figure 6B:
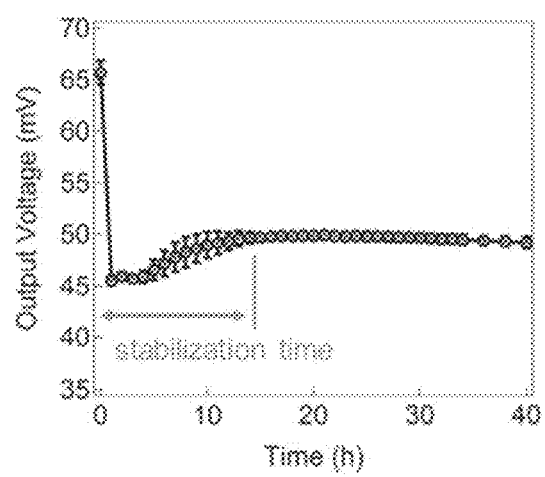

In another embodiment, the use of ion selective polymers in the salt bridge to reduce ion transport and improve measurement stability was explored. For example, polymers such as Nafion and polyDADMAC (polydiallyldimethylammonium chloride) have been tested (FIG. 6). In preliminary experiments, devices with ion selective polymers require several hours for stabilization. After the output voltage is stabilized, the test device has a constant output voltage for at least 20 hours.

Prototype Sweat Sensor and On-Body Tests

One example of the fabrication process is described in FIG. 7.

Figure 7A:
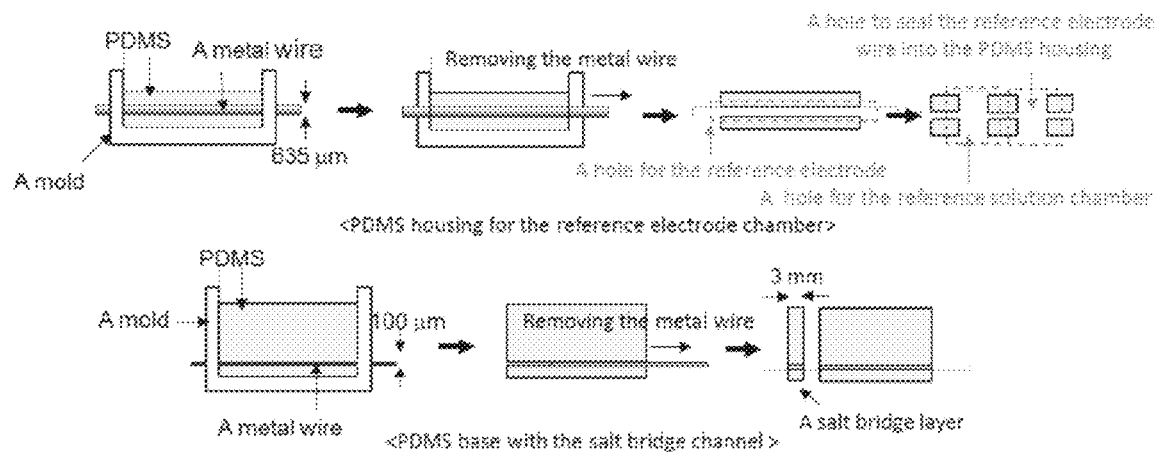
FIGS. 7A-7G. Fabrication process of the prototype sweat sensor.

Step 1. Fabrication of the polydimethylsiloxane (PDMS) housing for the reference electrode chamber (FIG. 7*a*). The PDMS housing that contains the reference solution and the wire reference electrode is formed by a casting process. A metal wire is inserted into a mold that is then filled with PDMS. The metal wire serves as a template to form the hole in the PDMS housing into which the wire electrode is inserted. The PDMS is then cured at 75° C. for 1 hour. The wire is then removed and the PDMS housing removed from the mold. The wire diameter is dependent on the diameter of the reference electrode wire to be used, but is typically 635 The thickness of the PDMS housing is about 5 mm, but can be decreased to make the sensor dimensions smaller.

After removal of the PDMS housing from the mold, a hole punch is used to form the reference solution chamber. An additional hole is punched in the housing that is later used to seal the reference electrode wire into the housing. The diameter of the reference electrode chamber is typically about 5 mm, but can also be smaller to reduce the size of the sensor.

Step 2. Fabrication of the PDMS base with the salt bridge channel (FIG. 7*a*).

The PDMS base that contains the salt bridge channel is also formed by a similar casting process using a metal wire template. Typically a metal wire of 100 µm in diameter is used to form a cylindrical channel in PDMS. The PDMS with the template wire still in place are removed from the mold. Next the template wire is removed from the PDMS.

The PDMS is then cut into slices with a thickness that defines the length of the salt bridge. Each slice forms the base of a sensor with a hole that will be the salt bridge channel. Typically the thickness of the PDMS base is 3 mm. The wire diameter defines the diameter if the salt bridge channel and can be changed by using a different diameter template wire. The length of the salt bridge is dependent on the thickness of the slice cut from the PDMS block.

Figures 7B, 7C, 7D:
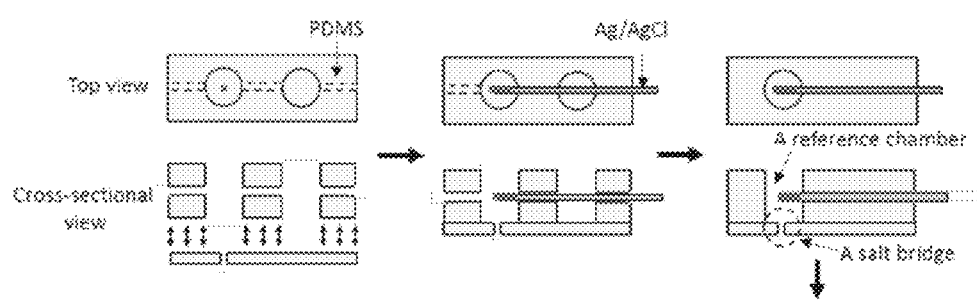

Step 3. The PDMS housing with the reference electrode chamber and PDMS base with the salt bridge channel are plasma bonded (FIG. 7b). A reference electrode (Ag/AgCl electrode) wire is inserted into the hole for the reference electrode (FIG. 7c).

Step 4. The second hole in the PDMS housing is then filled with PDMS to fix the reference electrode wire into the housing. The PDMS is then cured at 75° C. for 1 hour (FIG. 7d).

Figures 7E, 7F, 7G:
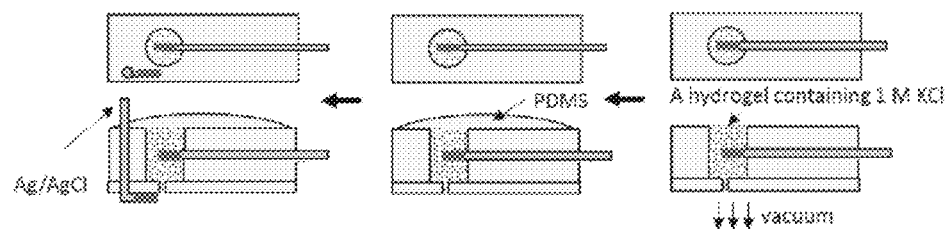

Step 5. The reference electrode chamber is filled with a hydrogel containing the reference solution. In many experiments, 1 M KCl in agarose was used (4% w/v ration agarose gel, 1 M KCl solution: agarose gel=20 ml: 0.8 g). Vacuum is applied to the chamber through the salt bridge channel to fill the salt bridge with the hydrogel (FIG. 7e). The gel in the reference electrode chamber containing the reference solution and the salt bridge are the same. The concentration of the reference solution and the composition of the gel in the reference chamber can be changed depending on the requirements.

Step 6. The top of the reference electrode chamber is sealed with PDMS. The device is placed in an oven at 45° C. for 5 hours to cure the PDMS on the top of the housing. The PDMS cap prevents evaporation of the reference solution in the reference chamber (FIG. 7f).

Step 7. Working electrode. A hole is formed in the housing for the working electrode using a 1 mm hole punch. A Ag/AgCl wire electrode is inserted into the hole (FIG. 7g).

Alternative Methods of Fabrication

Other methods for fabrication and other configurations have been developed. For example, in one embodiment, planar Ag/AgCl electrodes are used.

Figure 8A:
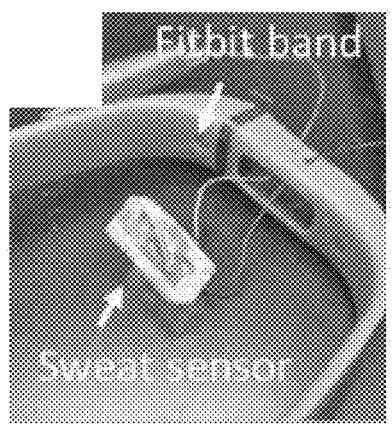
FIGS. 8A-8C. Photographs of the fabricated sweat sensor.
Figure 8B:
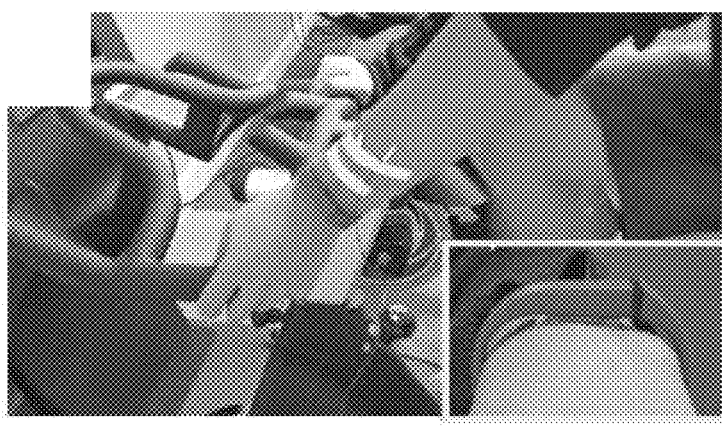
Figure 8C:
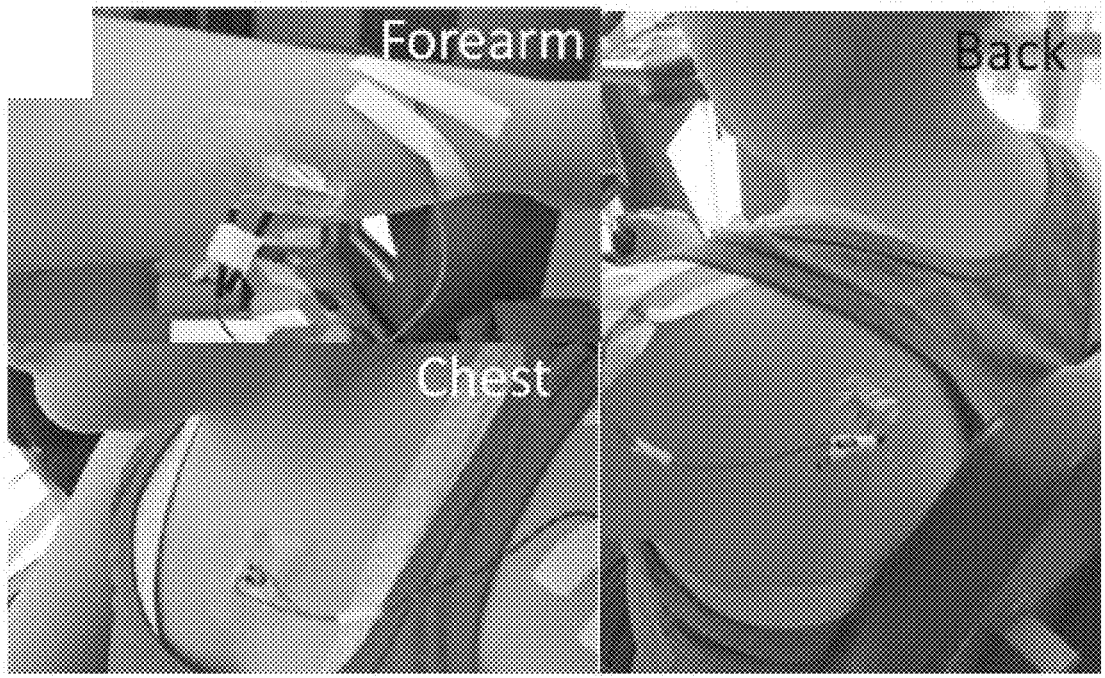

FIG. 8 (a-c) shows photographs of the fabricated sweat sensor. The device can be easily attached to the body using a wrist band from a fitness device (e.g., Fitbit, (FIG. 8b) or a commercial band aid (FIG. 8c).

On-body tests to monitor chloride concentration in sweat were performed. Three human subjects participated in these tests and did a constant-load exercise on an exercise bike for an hour. The devices were attached at various locations including forearm, chest, and back. The output voltage of the sensor was measured during the test by DAQ (data acquisition) systems and LABVIEW.

Figure 9A:
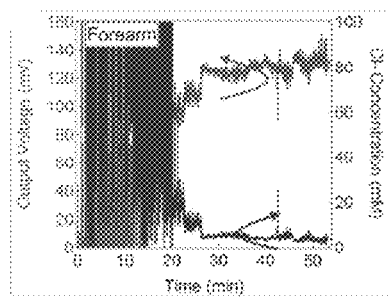
FIGS. 9A-9C. Simultaneous measurement of output voltage and chloride concentration measured at: (a) forearm, (b) chest, and (c) back.
Figure 9B:
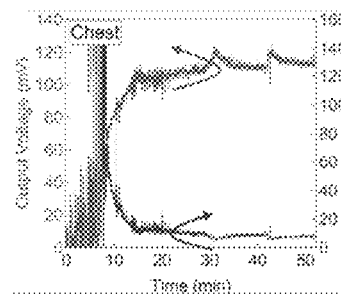
Figure 9C:
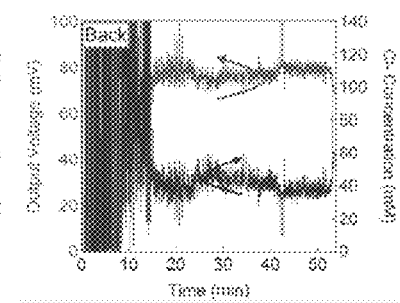

FIG. 9 shows output voltage and chloride concentration measured simultaneously at three different locations. Once the subject begins sweating a stable signal is measured.

The chloride concentrations measured during the exercise was in the range 5-40 mM, typical of a normal individual. Ten on-body tests with 14 sensors were performed, and the measured chloride concentrations are in the normal range (Table 1.)

TABLE 1

On-body test results (Subject 1: male, age = 35, height = 196 cm, weight = 100 kg, Subject 2: female, age = 19, height = 170 cm, weight = 60 kg, Subject 3: age = 28, height =155 cm, weight = 64.4 kg).

| Test | Subject | Position | Wearing Method | Perspiration Starting | Cl- Concentration |
|---|---|---|---|---|---|
| 1 | Subject 1 | Forearm | Fitbit band | <5 min | 25 mM |
| 2 | Subject 1 | Forearm | Fitbit band | <5 min | 20 mM |
| 3 | Subject 1 | Forearm | Fitbit band | 10 min | 25 mM |
| 4 | Subject 1 | Forearm | Fitbit band | 12 min | 38 mM |
| 5 | Subject 1 | Forearm | Fitbit band | <5 min | 20 mM |
|   |           |         | Band aid    | <5 min | 26 mM |
| 6 | Subject 1 | Forearm | Fitbit band | 12 min | 11 mM |
|   |           |         | Band aid    | 12 min | 12 mM |
| 7 | Subject 2 | Forearm | Fitbit band | 17 min | 10 mM |
| 8 | Subject 3 | Forearm | Fitbit band | 8 min  | 20 mM |
| 9 | Subject 3 | Forearm | Band aid    | 20 min | 4 mM |
|   |           | Chest   | Band aid    | 9 min  | 8 mM |
|   |           | Back    | Band aid    | 13 min | 40 mM |
| 10 | Subject 3 | Chest | Band aid    | 19 min | 8 mM |
|   |           | Back    | Band aid    | 22 min | 5 mM |

In this invention, to minimize a measurement error caused by transport of ions between the reference solution and the test solution (sweat), the salt bridge with an optimized geometry is adopted. To verify that the salt bridge can minimize the measurement error, the chloride concentration was compared to that obtained from a device fabricated to mimic the design in Gonzalo-Ruiz et al. 2009 and Lynch et al. 2002. FIG. 10a shows a schematic illustration of a device typical of those described in Gonzalo-Ruiz et al. 2009 and Lynch et al. 2002. Note that a similar design has been used to fabricate devices to measure sodium ions, ammonium ions (Gonzalo-Ruiz et al. 2009; Rose et al. 2015; Guinovart et al. 2013; Bandodkar et al. 2014). Calibration curves were obtained for both devices using known concentrations between 10 mM-100 mM. Both of the sensors were attached to the forearm with a band aid strip (FIG. 10b), and the output voltages were measured at the same time.

FIG. 10c shows the chloride concentration measured by the device described in this ROI and a device fabricated to mimic that described in Gonzalo-Ruiz et al. 2009 and Lynch et al. 2002. The concentration measured by the sensor designed to mimic the device described in Gonzalo-Ruiz et al. 2009 and Lynch et al. 2002 is much higher than that measured by the proposed device, which is caused by ion transport between the reference solution and the test solution (sweat). Since the chloride concentration of the reference solution (1 M KCl) is much higher than the sweat chloride concentration, the apparent sweat concentration increases.

Sensor Fabrication

Figure 15A:
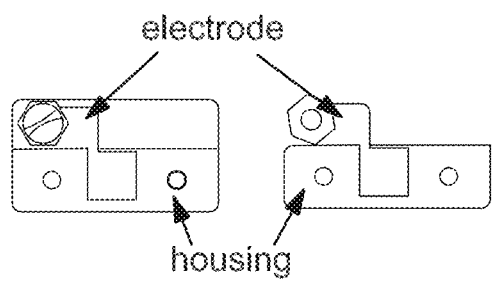
FIGS. 15A-15C. (A) Electrical connector for the sweat sensor. (B) Attaching the connector to the sensor. (C) The sensor assembled with the connector.
Figure 15B:
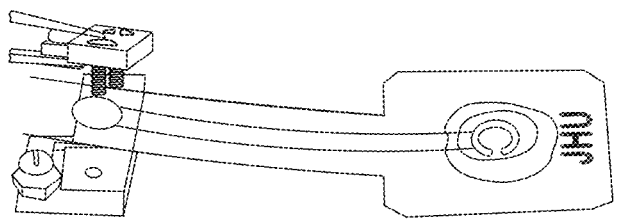
Figure 15C:
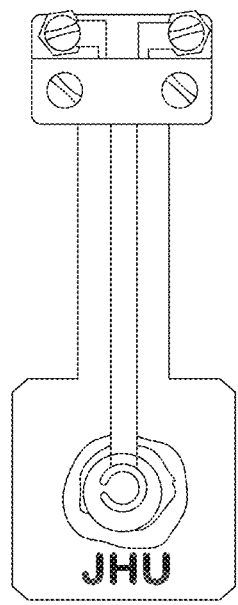

The sensor is fabricated on a 125 μm thick PET (Polyethylene terephthalate, Melinex® ST) film (FIG. 13). First, the salt bridge was defined by laser drilling a 30 μm in diameter hole in the PET film (FIG. 13A). To assess the role of salt bridge diameter on performance, sensors were also fabricated with salt bridge diameters of 500 μm and 1 mm. Next, a 10 nm Cr adhesion layer and a 300 nm Ag film were patterned on the top and bottom of the PET film by e-beam evaporation using shadow masks (FIG. 13B-C). Ag/AgCl electrodes were formed by incubating the patterned Ag electrodes in 25 μL of 50 mM $FeCl_3$ (Sigma-Aldrich) solution for 3 min (FIG. 13D). The Ag/AgCl electrodes on the top and bottom side serve as the reference and working electrodes, respectively. Next, approximately 200 μL of a 4 w/v % agarose gel (Invitrogen) containing 1 M KCl (Sigma Aldrich) solution was injected onto the reference electrode and the salt bridge hole (FIG. 13E). In this step, vacuum was applied to the hole to ensure complete filling with the gel. Finally, the gel was covered by a UV curable resin (Addison Clear Wave Coating, AC A 1450) (FIG. 13F). The resin was introduced on the gel using a syringe, and then cured by UV exposure. The wearable potentiometric sweat sensor was fabricated on a plastic PET substrate. The fabrication process is relatively simple and cost-effective, and involves laser drilling, e-beam evaporation and UV exposure processes (FIG. 13). To connect the sweat sensor to the data acquisition board (USB-6363, National Instruments) to measure the output voltage, an electrical connector was manufactured using 3D printing and machining (FIG. 15). The connector consists of two electrodes with screw terminals and a plastic housing (FIG. 15A-C).

Calibration of the Sweat Chloride Sensor

Calibration of the sensors was performed prior to all measurements. All devices were calibrated in the following way: (1) the working electrode was rinsed in running deionized (DI) water for 40 s, (2) 100 µL of 10 mM NaCl (Fisher Scientific) solution was placed on the working electrode of the sensor using a micropipette, (3) the sensor voltage was measured and recorded for 3 minutes, (4) steps 1-3 were repeated with 50 and 100 mM NaCl solutions, (5) the sensor voltage for each solution was determined by averaging the recorded voltages over last 1 min, and (6) using a linear least squares fit (V-log C), the relationship between the measured voltage and the concentration of the test solution was established. All calibrations were performed at room temperature. The output voltage of the sensors was measured and recorded by a data acquisition (DAQ) system (USB-6363, National Instruments) and Labview software (National Instrument).

Role of the Salt Bridge on Sensor Performance

To assess the influence of the salt bridge on performance, sensors were fabricated with 30 µm, 500 µm, and 1 mm diameter holes and their output voltages measured for 2 hours in contact with 110 µL of 10 mM NaCl solution. To prevent evaporation of the test solution, the sensor was mounted in a custom chamber, and the edges of the sensor sealed with Kapton tape (Uline). The chamber was fabricated from a 2.2 mm thick PDMS (polydimethylsiloxane, Sylgard 184, Dow Corning) film with an 8 mm diameter hole. The PDMS film was prepared by a conventional curing process (75° C. in a convection oven for 1 hour), and the hole was punched manually. A glass slide was then oxygen plasma bonded to one side of the PDMS film.

Device Accuracy

To assess device accuracy, the chloride concentration determined from the sensor measurement was compared to the known values of the test solutions in the concentration range 10-150 mM. Each test solution was prepared independently, and not from a diluted stock solution. The procedure was as follows: (1) a sensor was calibrated as described in Section 2.2, (2) 100 µL of a test solution was introduced onto the working electrode using a micropipette, (3) the sensor voltage was measured for 5 min. and the average sensor voltage determined for the last 1 minute, (4) the sensor working electrode was rinsed for 40 s using DI water and the measurement repeated with a new test solution. The measured voltages were converted to concentration values using the calibration curve, and the measured concentration compared to the concentration of the test solution.

Dose Response Curves

To assess the sensor performance in real time, dose response curves were obtained in the following way. A sensor was partially immersed into 100 mL of DI water so that the working electrode was completely submerged. Then, 1 mL of 1 M KCl solution was added to the solution every minute, and the output voltage was continuously recorded. To ensure good mixing, the test solution was agitated using a stirring bar.

On-Body Tests

On-body tests with a healthy subject while exercising on a stationary bike were performed in compliance with a protocol approved by the institutional review board (IRB) at Johns Hopkins University (HIRB00004232). Tests were performed at a constant load or with three incrementally increasing loads. The sensor was attached to the middle of the flexor aspect of the forearm with a commercial adhesive bandage (Nexcare, Tegaderm™). Before attaching the sensor, the area on the forearm was swabbed with alcohol and DI water. Prior to the test, the subject was asked to spin on a stationary bike at 45 W for 10 min as a warm-up. For the constant load test, the subject was asked to spin on the exercise bike at 100 W for one hour. During the test, the sensor voltage was continuously monitored. For the graded load test, the subject was asked to spin sequentially at 100, 125, and 150 W for 30 min, 15 min and 15 min, respectively. Each test was performed three times on different days. Each sensor was calibrated at room temperature (22° C.) before each test. The skin temperature during on-body tests was typically around 32° C., and the differences in sensor voltage between 22° C. and 32° C. ($V_{32° C.} - V_{22° C.}$) were verified to be in agreement with the values predicted by the Nernst equation. Therefore, all calibration curves were recorded at room temperature and adjusted for skin temperature using the Nernst equation. A paired-sample Students' t-test was performed to check the dependency of the sweat chloride concentration on the exercise load (* indicates p<0.05).

Influence of Temperature on Sensor Calibration

The voltage of a potentiometric sensor is dependent on temperature. According to the Nernst equation, the voltage of a potentiometric chloride sensor is given by:

$$V = -2.303 \frac{RT}{F} \log \frac{a_{Cl^-}^{sweat}}{a_{Cl^-}^{ref}}$$

where R is the gas constant, F is Faraday's constant, T is temperature, $a_{Cl^-}^{sweat}$ is the activity of chloride ion in sweat and $a_{Cl^-}^{ref}$ is the activity of chloride in the reference solution. The mean ionic activity coefficients ($\gamma_\pm$) for 10, 50, 100 NaCl are 0.903, 0.822, and 0.779, respectively. The mean ionic activity coefficient for 1 M KCl solution is 0.604.

Figure 17:
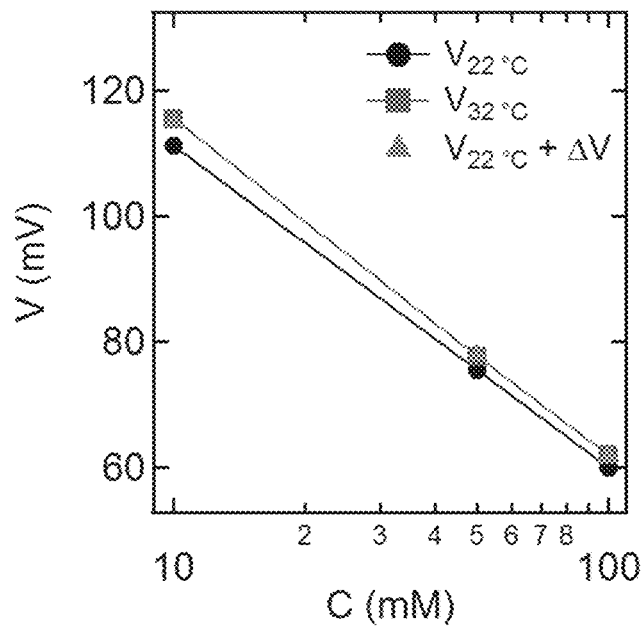
FIG. 17. Temperature dependence of sensor voltage. Calibration curves were measured at 22 (black circles) and 32° C. (blue squares). The sensor voltage at 32° C. predicted by the Nernst equation and the voltage at 22° C. (red triangles) are very close to the measured values (blue squares).

The sensors in this study were pre-calibrated at room temperature (22° C.), however, the skin temperature during on-body was about 32° C. To assess the influence of temperature on sensor voltage, calibration curves at 32° C. were measured (FIG. 17). The difference in sensor voltage between 22° C. and 32° C. ($\Delta V = V_{32° C.} - V_{22° C.}$) were 4.3, 2.2 and 2.0 mV in 10, 50, and 100 mM NaCl solution, respectively. The differences predicted by the Nernst equation are 3.7, 2.4, and 1.8 mV, in 10, 50, and 100 mM NaCl solution. Therefore, the small measured shift in the sensor voltage between room temperature and skin temperature is very close to the values predicted by the Nernst equation. Therefore, for the on-body tests, calibration curves were recorded at room temperature and adjusted for skin temperature using the Nernst equation.

Thin Film Sweat Chloride Sensor

Figure 14A:
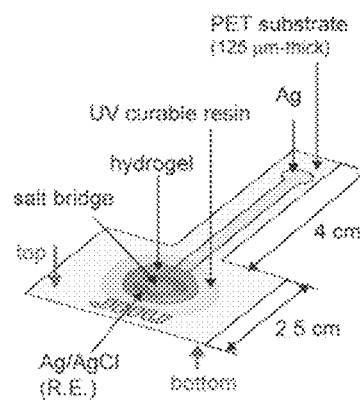
FIGS. 14A-14F. Thin film potentiometric chloride sensor with integrated salt bridge. (A) Schematic illustration of the sensor. (B) Top side (R.E.—reference electrode). (C) Bottom side (W.E.—working electrode). (D) Cross-section view of the sensor. (E) Optical image of the sensor after fabrication. (F) A sensor attached on the forearm using a transparent adhesive bandage.
Figure 14B:
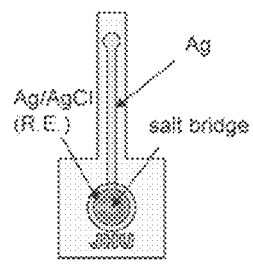
Figure 14C:
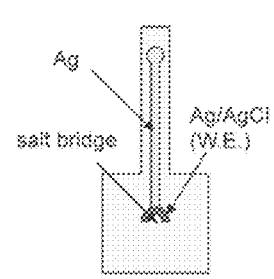
Figure 14D:
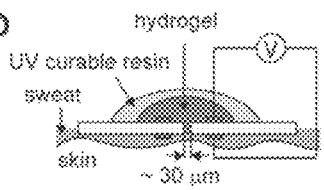
Figure 14E:
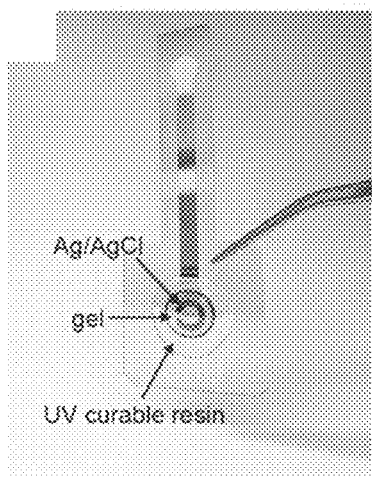
Figure 14F:
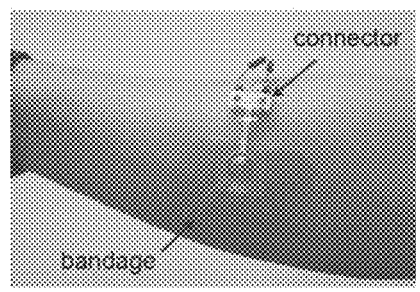

The wearable potentiometric sensor consists of planar Ag/AgCl reference and working electrodes located on opposite sides of a PET film and connected by a laser drilled hole that defines the salt bridge (FIG. 14A). The reference chamber consists of an agarose gel containing 1 M KCl and sealed with a UV curable resin to prevent evaporation of the reference solution in the hydrogel (FIG. 14B). The working electrode is formed on the bottom side of the PET film and directly contacts the skin when attached to the body (FIG. 14C). The main role of the salt bridge is to provide an ionic path between the reference and test solutions (FIG. 14D), however, the salt bridge geometry also determines the rate of equilibration between the reference and test solutions, and hence determines the time over which accurate measurements can be made. The sensor was fabricated by conventional thin film deposition processes (FIG. 14E) and the sensor was easily attached to the body using an adhesive bandage (FIG. 14F). For all measurements the sensor was connected to a data acquisition (DAQ) system (FIG. 15).

Calibration and Reproducibility

Figure 16A:
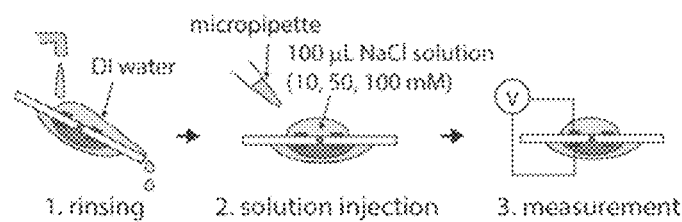
FIGS. 16A-16D. Sensor calibration and reproducibility. (A) Schematic illustration of the calibration procedure. All devices were calibrated three times following this procedure. (B) Sensor voltage versus time for three trials of a single device. (C) Calibration curve for multiple sensors (N=6). Data represent mean±SD (red dots: measured voltages, solid line: calibration curve obtained by the linear regression). Inset shows sensor voltage versus activity of the test solution (red dots: sensor voltages taking the junction potential into account, solid line: Nernst equation). (D) Measurement accuracy (ζ) due to variation among multiple sensors. The measurement accuracy was obtained by substituting the measured voltage (V) into the calibration curve (inset).
Figure 16B:
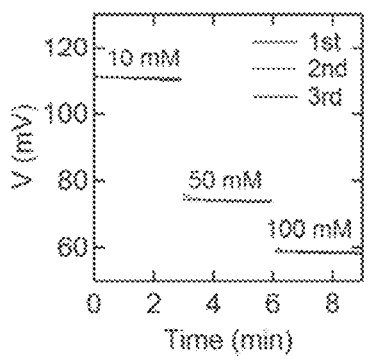
Figure 16C:
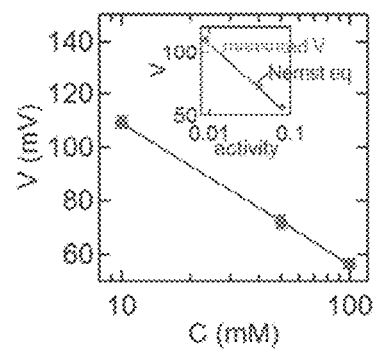

Devices were calibrated in test solutions of 10, 50, and 100 mM NaCl (FIG. 16A), spanning the range of healthy individuals and individuals with cystic fibrosis. A typical result from three sequential trials of a single sensor shows stable and reproducible values with voltage variations of less than 1 mV for each concentration (FIG. 16B). The average calibration curve (V vs. log C) obtained from multiple sensors (N=6) shows a slope of 52.8±0.7 mV decade-1 (FIG. 16C).

To compare the slopes of the calibration curves to the Nernst equation, the activity coefficients need to be taken into account. The activity coefficients are significantly less than 1.0 at the concentrations reported here: =0.903 for 10 mM NaCl, =0.822 for 50 mM NaCl, =0.779 for 100 mM NaCl), and =0.604 for 1 M KCl (reference solution). In addition, for the sensor configuration described here, the junction potential lowers the measured potential by about 2.0 mV. Replotting the sensor voltage versus activity and taking into account the junction potential, the slope of the calibration curves is 58.5 mV, identical to the theoretical value of 58.5 V predicted by the Nernst equation at 22° C. (FIG. 16C inset).

Figure 16D:
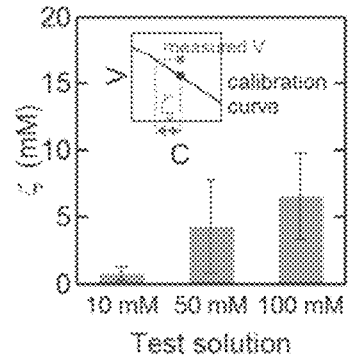

The deviation in sensor voltage from the average values (FIG. 16C) corresponds to an average variation in chloride concentration of less than 1 mM in 10 mM NaCl solution and about 6 mM in 100 mM NaCl solution (FIG. 16D). The maximum variation of 2.5 mV in 100 mM NaCl solution, corresponds to an error of 10 mM. The relatively small variation between sensors (FIG. 16D) indicates that each sensor does not need to be calibrated prior to use, depending on the desired accuracy of the measurement, significantly reducing time and cost.

Junction Potential

A junction potential $V_{junction}$ is developed at the interface between liquids with different ion compositions. The junction potential between the test solution and the salt bridge which has the same composition as the reference solution, was calculated from the Henderson equation:

$$V_{junction} = V_{TS} - V_{SB} = \frac{RT}{F} \frac{\sum_{i=1}^{N} z_i u_i (a_i^{TS} - a_i^{SB})}{\sum_{i=1}^{N} z_i^2 u_i (a_i^{TS} - a_i^{SB})} \ln \left( \frac{\sum_{i=1}^{N} z_i^2 u_i a_i^{TS}}{\sum_{i=1}^{N} z_i^2 u_i a_i^{SB}} \right)$$

where $V_{TS}$ is the potential of the test solution, $V_{SB}$ is the potential of the salt bridge (reference solution), R is the gas constant, T is temperature, F is Faraday's constant, $z_i$ is the valency of ion i, $u_i$ is mobility, and $a_i$ is activity. N is total number of ions in all solutions and the superscripts of TS and SB refer to test solution and salt bridge, respectively. The relative mobility $u_{Cl-}/u_{K+}=1.036$ and $u_{Na+}/u_{K+}=0.677$ at 22° C.

The calculated junction potentials at 22° C. in 10, 50 and 100 mM NaCl test solutions and 1 M KCl reference solution are −1.8, −0.5 and 0.3 mV, respectively. The calculated junction potentials at 32° C. in 10, 50 and 100 mM NaCl test solutions and 1 M KCl reference solution are −1.7, −0.4 and 0.3 mV, respectively. The sensor potential $V=V_{Nernst} V_{junction}$.

The Role of the Salt Bridge on Sensor Performance

Figure 19A:
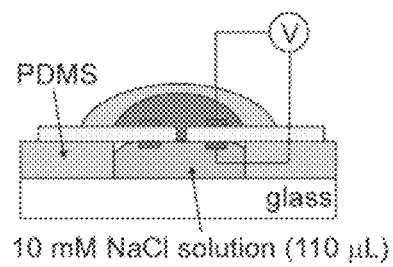
FIG. 19A-19D. The role of the salt bridge in sensor performance. (A) Schematic illustration of measurement set-up. (B) Measured output voltage versus time for sensors with salt bridge diameters of 30 μm, 500 μm, or 1 (N=3). (C) Chloride concentration versus time (N=3). (D) Chloride ion concentration for sensors with a 30 μm diameter salt bridge measured over 12 hours.
Figure 19B:
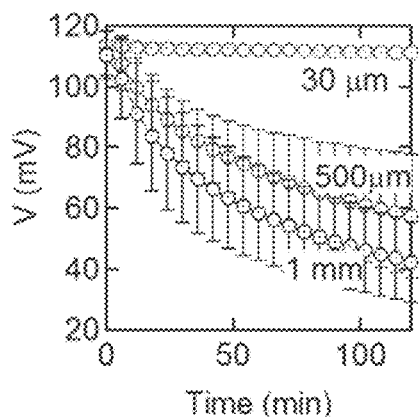
Figure 19C:
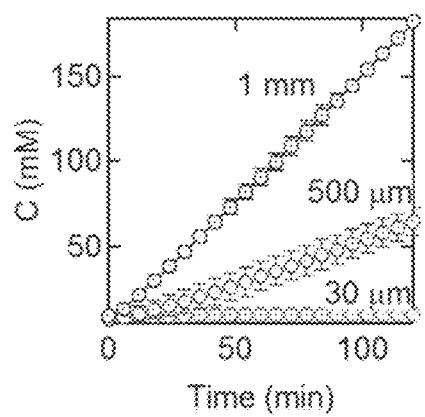

To assess the role of the salt bridge on performance, sensors were fabricated with salt bridge diameters of 30 μm, 500 μm or 1 mm. The length of the salt bridge is defined by the thickness of the PET substrate (125 μm). The sensors were mounted in a holder with 110 μL of 10 mM NaCl (FIG. 19A). For sensors with a 30 μm diameter salt bridge, the sensor voltage remained stable over 2 hours, but decreased rapidly with salt bridge diameters of 500 μm and 1 mm (FIG. 19B). The output voltages were converted to chloride ion concentrations using the calibration curve for each sensor (FIG. 19B). The measured concentration for sensors with a 30 μm diameter salt bridge remains very close to the concentration of the test solution (10 mM) over the 2 hour duration. In contrast, the sensors with 500 μm and 1 mm diameter salt bridges show a rapid increase in apparent chloride ion concentration over the same period. For a 500 μm salt bridge, the apparent concentration is about 64 mM after 2 hours.

The changes in sensor voltage and the corresponding chloride ion concentration are due to equilibration between the reference and test solutions. The concentration of the reference solution (1 M) is much larger than the test solution (10 mM), and hence the changes are dominated by the concentration change in the test solution. Since the concentration change is dependent on the volume of the test solution, the equilibration problem is more significant when the test (sweat) volume is very small. These results illustrate the important role of the salt bridge in potentiometric chloride sweat sensors.

Figure 19D:
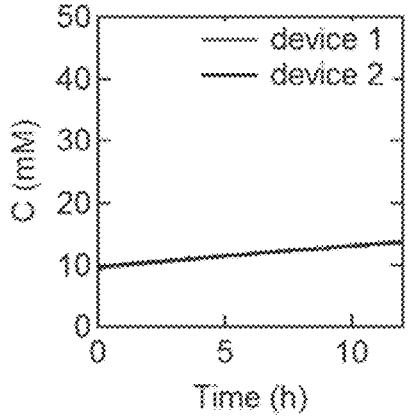

To test the long-term performance of sensors with a 30 μm diameter salt bridge, the sensor output over 12 hours with 110 μL of the test solution was recorded (FIG. 19D). The measured chloride ion concentration increased to 14 mM over 12 hours, a drift rate of about 0.3 mM $h^{-1}$. The relevance of these results to on-body tests and the sweat volume under the sensor are discussed in "Sweat volume under the sensor and concentration drift rate (Q)".

Sweat Volume Under the Sensor and Concentration Drift Rate (Q)

Figure 18A:
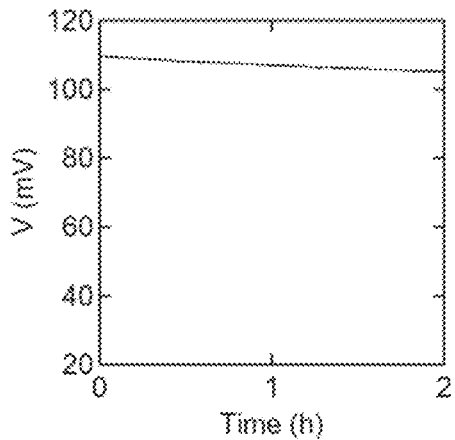
FIG. 18A-18B. Sensor measurement in 20 μL of 10 mM NaCl. (A) Voltage and (B) concentration for a sensor with a 30 μm diameter salt bridge over 2 hours.
Figure 18B:
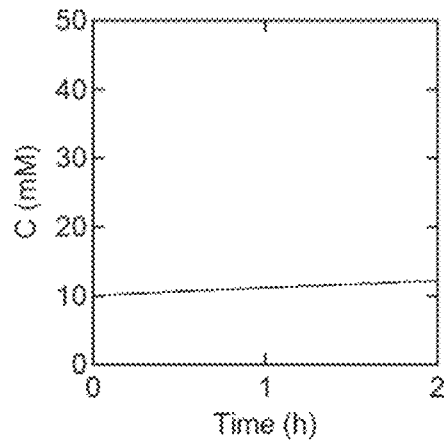

The groves in skin have a depth of about 40 μm and the androgenic (body) hair on forearm is about 30 μm in diameter. Assuming the gap between the sensor and skin is 30 μm, the sweat volume (v) under the sensor (the sensing area is 2.5 cm by 2.5 cm) is about 20 μL. To estimate the maximum measurement error during on-body tests, the sensor voltage in a test solution volume of 20 μL of 10 mM NaCl for 2 hours was recorded. The concentration increase was about 2.2 mM for 2 hours (FIG. 18), corresponding to a concentration drift rate Q of about 1.1 mM $h^{-1}$ which is 3.7 times larger than Q value of 0.3 mM $h^{-1}$ at v=110 μL. In practice, with a continuous sweat generation rate, sweat will flow out of the region under the sensor onto the skin. A typical sweat generation rate of 1 µL cm$^{-2}$ min$^{-1}$ would result in 750 µL sweat under the sensor (2.5 cm×2.5 cm) in 2 hours, much larger than the 20 µL in this test. Therefore, the concentration drift rate during the 2 hour on-body tests is expected to be negligible for the salt bridge geometry and sensor design employed here.

Measurement Accuracy and Dose Response

Figure 20A:
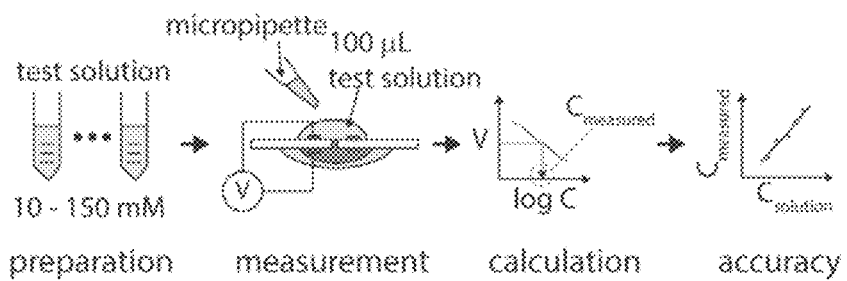
FIGS. 20A-20C. Measurement accuracy. (A) Procedure for testing measurement accuracy. (B) Concentration obtained from the sensor versus known test solution concentration. As a guide, the dotted lines show ±5 mM. (C) Chloride concentration obtained from the sensor for a test solution concentration of 150 mM over repeated measurements. The dotted line represents 150±5 mM. The inset shows the sensor voltage and the solid line represents voltage corresponding to 150 mM.
Figure 20B:
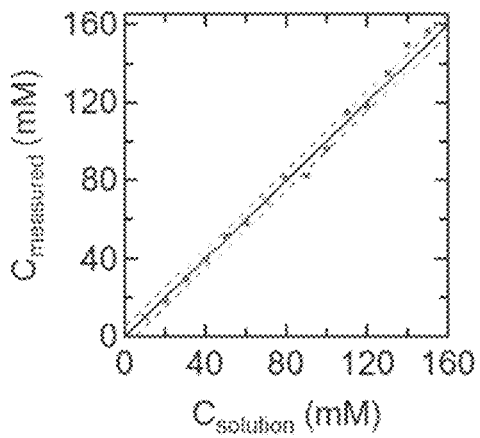

To further evaluate measurement accuracy and sensor performance, test solutions over the concentration range 10-150 mM were measured (FIG. 20A). One hundred µL of the test solution was placed on the working electrode of the sensor using micropipette, and the concentration of the test solution obtained from the sensor voltage and calibration curve. The concentration determined from the sensor and the known concentration of the test solution are in excellent agreement with a Pearson correlation coefficient of 0.9968 (FIG. 20B). The measurement accuracy is 0.13 mM in 10 mM solution and increases to 4.7 mM in 150 mM solution. The accuracy decreases as the concentration of the test solution increases since the output voltage is inversely proportional to log C.

Figure 20C:
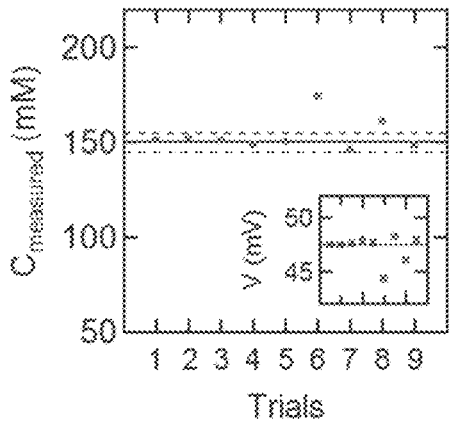

To assess reproducibility, the chloride ion concentration was measured repeatedly in 150 mM solution (FIG. 20C) following sensor calibration. The average sensor voltage was 47.2±1.2 mV (mean±standard deviation) and from the calibration curve an average variation of 5.3±8 mM is obtained. As described above, for low chloride ion concentrations, variations in sensor voltage can be ignored. For example, for a 10 mM test solution, a 5 mV variation in sensor voltage corresponds to a concentration difference of 2 mM (for a 53 mV decade$^{-1}$ calibration curve). However, as the concentration of the test solution increases, the measurement error caused by the sensor voltage variation cannot be ignored. For example, the difference between the measured. and calibration voltages in the sixth trial in 150 mM solution (FIG. 20C) is only 3 mV, but the concentration measurement error is 25 mM.

Figure 21A:
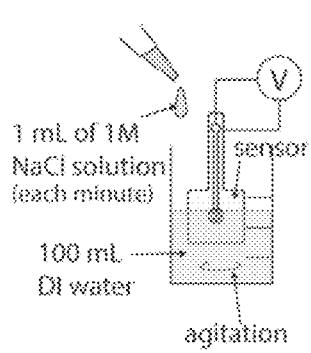
FIGS. 21A-21C. Dose response curve. (A) Measurement set-up. The test solution was initially 100 mL of DI water. 1 mL of 1 M NaCl solution was added to the water every single minute. (B) Dose response curve. (C) Measured concentration and calculated test solution concentration of the test solution.
Figure 21B:
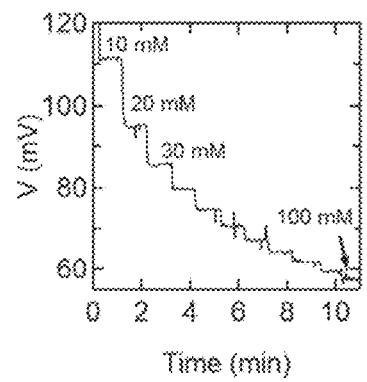
Figure 21C:
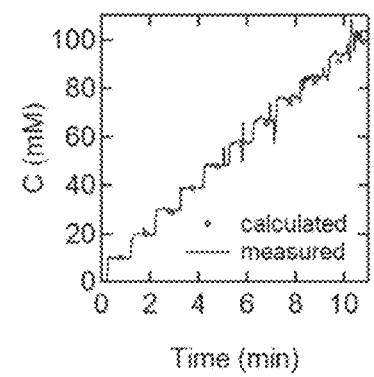

To assess the sensor response time, dose response curves were recorded. 1 mL of 1 M NaCl solution was pipetted every minute into 100 mL of DI water, and the output voltage of the sensor was recorded as a function of time (FIG. 21A). From the dose response curves (FIG. 21B) a response time constant of about 2 s at all concentrations was obtained. The concentration obtained from the sensor is in good agreement with the calculated concentration (FIG. 21C), and the variation was below 5 mM.

Figure 22A:
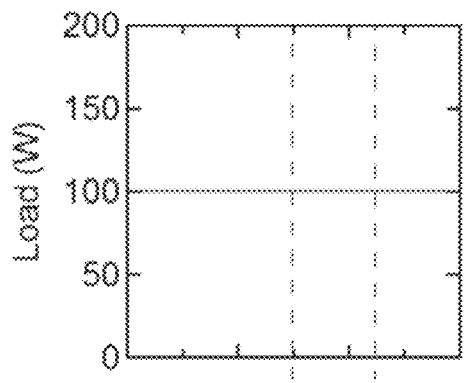
FIGS. 22A-22F. On-body tests for a healthy individual while exercising. (A) Exercise profile for constant load test. (B) Representative sweat chloride measurement. (C) Sweat chloride concentrations at t=30, 45 and 60 min (N=3). Bars represent mean±SE. (D) Exercise profile for graded load test. (E) Measured sweat chloride concentration. (F) Sweat chloride concentration at t=30, 45, and 60 mins (N=3). Bars represent mean±SE (* $p<0.05$).
Figure 22D:
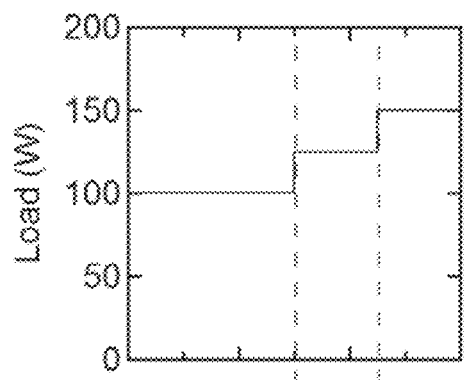
Figure 22B:
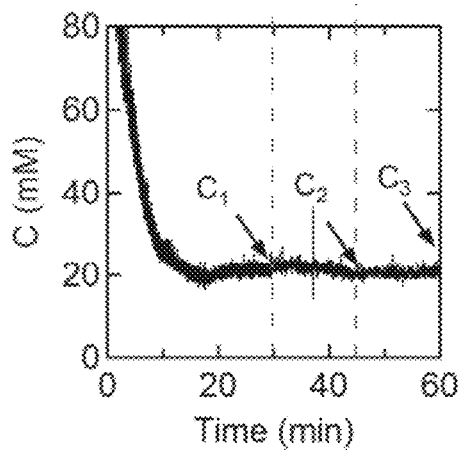

To assess sensor performance, trials were performed with a healthy subject while exercising on a stationary bike. Two types of tests were performed. In the first set of trials, the subject was requested to spin at constant power (100 W) for 60 minutes (FIG. 22A). In the second set of trials, the subject was requested to increase the power after 30 minutes and again after 45 minutes (FIG. 22D). In general, the onset of sweating occurred after 15-20 minutes, at which point a stable chloride ion concentration was measured (FIG. 22B, E).

Figure 22E:
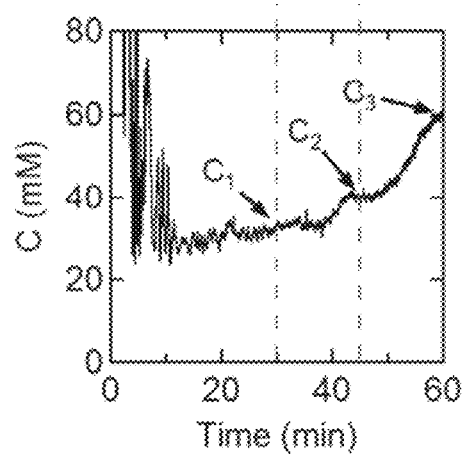
Figure 22C:
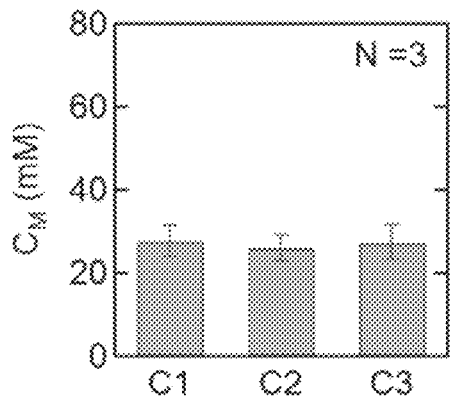
Figure 22F:
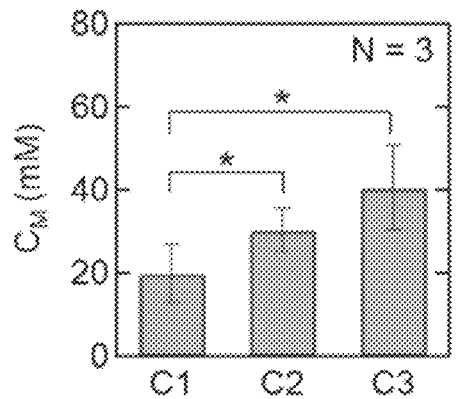

At constant exercise load, the measured chloride concentrations were in the normal range for healthy individuals (10-40 mM). To assess changes in the sweat concentration during the test, values at 30 ($C_1$), 45 ($C_2$), and 60 minutes ($C_3$) were compared (FIG. 22C). There was no statistical difference in sweat chloride as a function of time.

To assess the role of exercise intensity on sweat chloride concentration, a graded exercise load test was performed (FIG. 22D). In contrast to exercise at constant load, the sweat concentration increased in response to an increase in exercise intensity (FIG. 22E, F). The chloride concentration in sweat is known to increase with increasing sweat rate when the sweat rate exceeds the absorption rate of the sweat gland (Dill et al. 1966; Emrich et al. 1968). Therefore, the increase in sweat chloride with exercise intensity is likely due to an increase in sweat rate.

In sum, a thin film, potentiometric sweat chloride sensor with integrated salt bridge was fabricated and tested. The salt bridge minimizes equilibration between the reference solution and sweat sample and enables stable measurements over extended periods of time. The sensor showed a very small concentration drift (<4 mM) over 12 hours even though the volume of the test solution was only 110 µL. The measurement variation was less than 2 mM at low chloride ion concentration (10 mM) and 5 mM at high concentration (150 mM), spanning the range for healthy individuals and CF patients, typically 10-150 mM, and hence the device could be used as a diagnostic tool for CF. In on-body tests, the sweat chloride concentration in healthy individuals was shown to be dependent on exercise intensity, indicating that the sensor has a potential for a fitness monitoring applications Applications This sensor can be used as a wearable sensor to monitor sweat concentration of CF (cystic fibrosis) patients.

One current technology, the Macroduct® Sweat Collection System (ELITech Group) includes (1) Webster sweat inducer that administers pilocarpine using iontophoresis (FIG. 11a), and (2) Macroduct collector to collect the sweat induced by iontophoresis (FIG. 11b). The collected sweat is then sent to a lab for analysis. Macroduct® Sweat Collection System is commonly used in a hospital to collect sweat for CF diagnosis. The proposed sensor could be used to replace the Macroduct collector (FIG. 11b) to enable measurement of the chloride concentration in the clinic, without having to send the sample to the lab for analysis.

This wearable chloride sensor could also be used to measure electrolyte balance during workouts and hence could be integrated into a fitness sensor.

REFERENCES

The following references are each relied upon and incorporated herein in their entirety.

Bandodkar, A. J., Molinnus, D., Mirza, O., Guinovart, T., Windmiller, J. R., Valdes-Ramirez, G., Andrade, F. J., Schoning, M. J., Wang, J., 2014. Epidermal tattoo potentiometric sodium sensors with wireless signal transduction for continuous non-invasive sweat monitoring. Biosens Bioelectron 54, 603-609.

Barben, J., Ammann, R. A., Metlagel, A., Schoeni, M. H., Swiss Paediatric Respiratory Research, G., 2005. Conductivity determined by a new sweat analyzer compared with chloride concentrations for the diagnosis of cystic fibrosis. J Pediatr 146(2), 183-188.

Barry, P. H., Lewis, T. M., Moorhouse, A. J., 2013. An optimised 3 M KCl salt-bridge technique used to measure and validate theoretical liquid junction potential values in patch-clamping and electrophysiology. Eur Biophys J 42(8), 631-646.

Choi, D.-H., Kim, J. S., Cutting, G. R., Searson, P. C., 2016. Wearable Potentiometric Chloride Sweat Sensor: The Critical Role of the Salt Bridge. Analytical Chemistry 88(24), 12241-12247.

Costill, D. L., Cote, R., Fink, W., 1976. Muscle water and electrolytes following varied levels of dehydration in man. J Appl Physiol 40(1), 6-11.

Coury, A. J., Fogt, E. J., Norenberg, M. S., Untereker, D. F., 1983. Development of a screening system for cystic fibrosis. Clin Chem 29(9), 1593-1597.

Dam, V. A. T. Z., M. A. G.; van Schaijk, R., 2016. Toward wearable patch for sweat analysis. Sensors and Actuators B: Chemical 236(29), 5.

Dill, D. B., Hall, F. G., Van Beaumont, W., 1966. Sweat chloride concentration: sweat rate, metabolic rate, skin temperature, and age. J Appl Physiol 21(1), 99-106.

Dussaud, A. D., Adler, P. M., Lips, A., 2003. Liquid transport in the networked microchannels of the skin surface. Langmuir 19(18), 7341-7345.

Emrich, H. M., Stoll, E., Friolet, B., Colombo, J. P., Richterich, R., Rossi, E., 1968. Sweat composition in relation to rate of sweating in patients with cystic fibrosis of the pancreas. Pediatr Res 2(6), 464-478.

Fernandes, A. D., Amorim, P. R. D., Brito, C. J., de Moura, A. G., Moreira, D. G., Costa, C. M. A., Sillero-Quintana, M., Marins, J. C. B., 2014. Measuring skin temperature before, during and after exercise: a comparison of thermocouples and infrared thermography. Physiol Meas 35(2), 189-203.

Gao, W., Emaminejad, S., Nyein, H. Y., Challa, S., Chen, K., Peck, A., Fahad, H. M., Ota, H., Shiraki, H., Kiriya, D., Lien, D. H., Brooks, G. A., Davis, R. W., Javey, A., 2016. Fully integrated wearable sensor arrays for multiplexed in situ perspiration analysis. Nature 529(7587), 509-514.

Gibson, L. E., Cooke, R. E., 1959. A test for concentration of electrolytes in sweat in cystic fibrosis of the pancreas utilizing pilocarpine by iontophoresis. Pediatrics 23(3), 545-549.

Gonzalo-Ruiz, J., Mas, R., de Haro, C., Cabruja, E., Camero, R., Alonso-Lomillo, M. A., Munoz, F. J., 2009. Early determination of cystic fibrosis by electrochemical chloride quantification in sweat. Biosens Bioelectron 24(6), 1788-1791.

Hamer, W. J., Wu, Y.-C., 1972. Osmotic coefficients and mean activity coefficients of uni-univalent electrolytes in water at 25° C. Journal of Physical and Chemical Reference Data 1(4), 1047-1100.

Bandodkar, A. J., Molinnus, D., Mirza, O., Guinovart, T., Windmiller, J. R., Valdes-Ramirez, G., Andrade, F. J., Schoning, M. J., Wang, J., 2014. Epidermal tattoo potentiometric sodium sensors with wireless signal transduction for continuous non-invasive sweat monitoring. Biosens Bioelectron 54, 603-609.

Barben, J., Ammann, R. A., Metlagel, A., Schoeni, M. H., Swiss Paediatric Respiratory Research, G., 2005. Conductivity determined by a new sweat analyzer compared with chloride concentrations for the diagnosis of cystic fibrosis. J Pediatr 146(2), 183-188.

Barry, P. H., Lewis, T. M., Moorhouse, A. J., 2013. An optimised 3 M KCl salt-bridge technique used to measure and validate theoretical liquid junction potential values in patch-clamping and electrophysiology. Eur Biophys J 42(8), 631-646.

Choi, D.-H., Kim, J. S., Cutting, G. R., Searson, P. C., 2016. Wearable Potentiometric Chloride Sweat Sensor: The Critical Role of the Salt Bridge. Analytical Chemistry 88(24), 12241-12247.

Costill, D. L., Cote, R., Fink, W., 1976. Muscle water and electrolytes following varied levels of dehydration in man. J Appl Physiol 40(1), 6-11.

Coury, A. J., Fogt, E. J., Norenberg, M. S., Untereker, D. F., 1983. Development of a screening system for cystic fibrosis. Clin Chem 29(9), 1593-1597.

Dam, V. A. T. Z., M. A. G.; van Schaijk, R., 2016. Toward wearable patch for sweat analysis. Sensors and Actuators B: Chemical 236(29), 5.

Dill, D. B., Hall, F. G., Van Beaumont, W., 1966. Sweat chloride concentration: sweat rate, metabolic rate, skin temperature, and age. J Appl Physiol 21(1), 99-106.

Emrich, H. M., Stoll, E., Friolet, B., Colombo, J. P., Richterich, R., Rossi, E., 1968. Sweat composition in relation to rate of sweating in patients with cystic fibrosis of the pancreas. Pediatr Res 2(6), 464-478.

Fernandes, A. D., Amorim, P. R. D., Brito, C. J., de Moura, A. G., Moreira, D. G., Costa, C. M. A., Sillero-Quintana, M., Marins, J. C. B., 2014. Measuring skin temperature before, during and after exercise: a comparison of thermocouples and infrared thermography. Physiol Meas 35(2), 189-203.

Gao, W., Emaminejad, S., Nyein, H. Y., Challa, S., Chen, K., Peck, A., Fahad, H. M., Ota, H., Shiraki, H., Kiriya, D., Lien, D. H., Brooks, G. A., Davis, R. W., Javey, A., 2016. Fully integrated wearable sensor arrays for multiplexed in situ perspiration analysis. Nature 529(7587), 509-514.

Gibson, L. E., Cooke, R. E., 1959. A test for concentration of electrolytes in sweat in cystic fibrosis of the pancreas utilizing pilocarpine by iontophoresis. Pediatrics 23(3), 545-549.

Gonzalo-Ruiz, J., Mas, R., de Haro, C., Cabruja, E., Camero, R., Alonso-Lomillo, M. A., Munoz, F. J., 2009. Early determination of cystic fibrosis by electrochemical chloride quantification in sweat. Biosens Bioelectron 24(6), 1788-1791.

Guinovart, Tomas et al, *Analyst,* 2013, 138, 7031-7038.

Hamer, W. J., Wu, Y.-C., 1972. Osmotic coefficients and mean activity coefficients of uni-univalent electrolytes in water at 25° C. Journal of Physical and Chemical Reference Data 1(4), 1047-1100.

Hammond, K. B., Turcios, N. L., Gibson, L. E., 1994. Clinical evaluation of the macroduct sweat collection system and conductivity analyzer in the diagnosis of cystic fibrosis. J Pediatr 124(2), 255-260.

Heikenfeld, J., 2016. Non-invasive Analyte Access and Sensing through Eccrine Sweat: Challenges and Outlook circa 2016. Electroanalysis 28(6), 8.

Kshirsagar, S. V. S., B.; Fulari, S. P., 2009. Comparative study of human and animal hair in relation with diameter and medullary index. Indian Journal of Forensic Medicine and Pathology 2(3), 105-108.

Latzka, W. A., Montain, S. J., 1999. Water and electrolyte requirements for exercise. Clin Sports Med 18(3), 513-524.

LeGrys, V. A., Yankaskas, J. R., Quittell, L. M., Marshall, B. C., Mogayzel, P. J., Jr., Cystic Fibrosis, F., 2007. Diagnostic sweat testing: the Cystic Fibrosis Foundation guidelines. J Pediatr 151(1), 85-89.

Lynch, Aogán et al. *Analyst,* 125 (2002) 2264-2267.

Macroduct sweat collection system, ELITechGroup.

Otberg, N. R., H.; Shaefer H.; Blume-Peytavi, U.; Sterry, W.; Lademann, J, 2004. Variation of Hair Follicle Size and Distribution in Different Body Sites. Journal of Investigative Dermatology 122, 14-19.

Quinton, P. M., 2007. Cystic fibrosis: lessons from the sweat gland. Physiology (Bethesda) 22, 212-225.

Robinson, S., Robinson, A. H., 1954. Chemical composition of sweat. Physiol Rev 34(2), 202-220.

Rock, M. J., Makholm, L., Eickhoff, J., 2014. A new method of sweat testing: the CF Quantum(R) sweat test. J Cyst Fibros 13(5), 520-527.

Rose, D. P., Ratterman, M. E., Griffin, D. K., Hou, L., Kelley-Loughnane, N., Naik, R. R., Hagen, J. A., Papautsky, I., Heikenfeld, J. C., 2015. Adhesive RFID Sensor Patch for Monitoring of Sweat Electrolytes. IEEE Trans Biomed Eng 62(6), 1457-1465.

Sonner, Z., Wilder, E., Heikenfeld, J., Kasting, G., Beyette, F., Swaile, D., Sherman, F., Joyce, J., Hagen, J., Kelley-Loughnane, N., Naik, R., 2015. The microfluidics of the eccrine sweat gland, including biomarker partitioning, transport, and biosensing implications. Biomicrofluidics 9(3), 031301.

Taylor, N. A., Machado-Moreira, C. A., 2013. Regional variations in transepidermal water loss, eccrine sweat gland density, sweat secretion rates and electrolyte composition in resting and exercising humans. Extrem Physiol Med 2(1), 4.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims

What is claimed is:

1. A potentiometric sweat sensor comprising:
   a substrate which has a through hole;
   a working electrode which is in contact with sweat on skin;
   a reference electrode, wherein the reference electrode is disposed above an upper surface of the substrate and at least a portion of the working electrode is disposed on a bottom surface of the substrate;
   a reference solution hydrogel disposed on the upper surface of the substrate, wherein the reference electrode is disposed at least partially within the reference solution hydrogel; and
   a salt bridge which is formed in the through hole, wherein one side of the salt bridge contacts the sweat on the skin and an opposing side of the salt bridge is in physical contact with the reference solution hydrogel, and wherein an ionic path between the reference electrode and the working electrode is formed through the salt bridge via the sweat.

2. The potentiometric sensor of claim 1, wherein the substrate is a flexible substrate.

3. The potentiometric sensor of claim 1, wherein the through hole overlaps with the reference hydrogel and does not vertically overlap with the working electrode.

4. The potentiometric sensor of claim 1, wherein the reference electrode comprises a conductive layer and a AgCl (silver chloride) layer, and wherein the conductive layer is interposed between the substrate and the AgCl layer.

5. The potentiometric sensor of claim 1, wherein the working electrode comprises a conducting part and a sensing part, and wherein the conducting part is interposed between the substrate and the sensing part.

6. The potentiometric sensor of claim 5, wherein sweat is in contact with the sensing part and an electrochemical equilibrium is established with a sweat component along the ionic path.

7. The potentiometric sensor of claim 6, wherein the sensing part detects chloride ions, and wherein the sensing part is a Ag/AgCl layer.

8. The potentiometric sensor of claim 1, wherein a reference solution in the reference solution hydrogel contains chloride ions.

9. The potentiometric sensor of claim 1, wherein the salt bridge contains a hydrogel or an ion selective polymer.

10. The potentiometric sensor of claim 1, wherein the reference solution hydrogel is covered by an encapsulation layer.

11. The potentiometric sensor of claim 10, wherein the encapsulation layer contains a UV curable resin or polymer.

* * * * *